(12) United States Patent
Amplatz et al.

(10) Patent No.: US 8,747,453 B2
(45) Date of Patent: Jun. 10, 2014

(54) STENT/STENT GRAFT FOR REINFORCEMENT OF VASCULAR ABNORMALITIES AND ASSOCIATED METHOD

(75) Inventors: Kurt Amplatz, St. Paul, MN (US); John C. Oslund, Blaine, MN (US); Patrick Russo, Vadnais Heights, MN (US); Xiaoping Gu, Maplewood, MN (US)

(73) Assignee: AGA Medical Corporation, Plymouth, MN (US)

( * ) Notice: Subject to any disclaimer, the term of this patent is extended or adjusted under 35 U.S.C. 154(b) by 0 days.

(21) Appl. No.: 12/032,944

(22) Filed: Feb. 18, 2008

(65) Prior Publication Data

US 2009/0210048 A1    Aug. 20, 2009

(51) Int. Cl.
 *A61F 2/06* (2013.01)
(52) U.S. Cl.
 USPC ............ 623/1.19; 623/1.18; 623/1.2; 623/1.3
(58) Field of Classification Search
 USPC ................ 623/1.13, 1.18–1.19, 1.2, 1.25, 1.3
 See application file for complete search history.

(56) References Cited

U.S. PATENT DOCUMENTS

| | | | |
|---|---|---|---|
| 3,834,388 A | 9/1974 | Sauer | |
| 3,874,388 A | 4/1975 | King et al. | |
| 4,304,010 A | 12/1981 | Mano | |
| 4,441,215 A | 4/1984 | Kaster | |
| 4,655,771 A | 4/1987 | Wallsten | |
| 4,728,328 A | 3/1988 | Hughes et al. | |
| 4,836,204 A | 6/1989 | Landymore et al. | |
| 4,917,089 A | 4/1990 | Sideris | |
| 4,991,602 A | 2/1991 | Amplatz et al. | |
| 5,064,435 A | 11/1991 | Porter | |
| 5,067,489 A | 11/1991 | Lind et al. | |
| 5,108,420 A | 4/1992 | Marks | |
| 5,334,217 A | 8/1994 | Das | |
| 5,522,822 A | 6/1996 | Phelps et al. | |
| 5,522,881 A | 6/1996 | Lentz | |
| 5,562,725 A | 10/1996 | Schmitt et al. | |
| 5,628,788 A | 5/1997 | Pinchuk | |
| 5,709,707 A | 1/1998 | Lock et al. | |
| 5,709,713 A | 1/1998 | Evans et al. | |
| 5,725,552 A | 3/1998 | Kotula et al. | |

(Continued)

FOREIGN PATENT DOCUMENTS

| | | |
|---|---|---|
| CA | 2501033 | 7/2008 |
| CN | 2524710 Y | 12/2002 |

(Continued)

OTHER PUBLICATIONS

Office Action for U.S. Appl. No. 12/040,260 dated Aug. 5, 2010.

(Continued)

*Primary Examiner* — Thomas J Sweet
*Assistant Examiner* — Seema Mathew
(74) *Attorney, Agent, or Firm* — Armstrong Teasdale LLP

(57) ABSTRACT

A stent/stent graft for reinforcement of vascular abnormalities and an associated method are provided. According to on embodiment, the stent/stent graft includes a flexible tubular structure comprising proximal and distal ends and having a heat set configuration. The tubular structure is configured to engage a lumen upstream and downstream of a vascular abnormality, such as an aneurysm, and a portion between the proximal and distal ends of the tubular structure is configured to engage the aneurysm.

38 Claims, 4 Drawing Sheets

(56) References Cited

U.S. PATENT DOCUMENTS

| | | |
|---|---|---|
| 5,741,325 A | 4/1998 | Chaikof et al. |
| 5,755,772 A | 5/1998 | Evans et al. |
| 5,758,562 A | 6/1998 | Thompson |
| 5,800,508 A | 9/1998 | Goicoechea et al. |
| 5,846,261 A | 12/1998 | Kotula et al. |
| 5,865,791 A | 2/1999 | Whayne et al. |
| 5,906,641 A | 5/1999 | Thompson et al. |
| 5,916,264 A | 6/1999 | Von Oepen et al. |
| 5,928,260 A | 7/1999 | Chin et al. |
| 5,944,738 A | 8/1999 | Amplatz et al. |
| 5,957,974 A | 9/1999 | Thompson et al. |
| 5,984,917 A | 11/1999 | Fleischman et al. |
| 5,994,738 A | 11/1999 | Wollesen |
| 6,042,592 A | 3/2000 | Schmitt |
| 6,059,812 A | 5/2000 | Clerc et al. |
| 6,066,776 A | 5/2000 | Goodwin et al. |
| 6,096,052 A | 8/2000 | Callister et al. |
| 6,110,198 A | 8/2000 | Fogarty et al. |
| 6,123,715 A | 9/2000 | Amplatz |
| 6,132,438 A | 10/2000 | Fleischman et al. |
| 6,152,144 A | 11/2000 | Lesh et al. |
| 6,156,064 A | 12/2000 | Chouinard |
| 6,168,615 B1 | 1/2001 | Ken et al. |
| 6,168,622 B1 | 1/2001 | Mazzocchi |
| 6,187,025 B1 | 2/2001 | Machek |
| 6,214,029 B1 | 4/2001 | Thill et al. |
| 6,241,768 B1 | 6/2001 | Agarwal et al. |
| 6,267,775 B1 | 7/2001 | Clerc et al. |
| 6,299,636 B1 | 10/2001 | Schmitt et al. |
| 6,346,117 B1 | 2/2002 | Greenhalgh |
| 6,368,339 B1 | 4/2002 | Amplatz |
| 6,379,366 B1 | 4/2002 | Fleischman et al. |
| 6,447,531 B1 | 9/2002 | Amplatz |
| 6,468,301 B1 | 10/2002 | Amplatz et al. |
| 6,468,303 B1 | 10/2002 | Amplatz et al. |
| 6,469,303 B1 | 10/2002 | Sun et al. |
| 6,475,227 B2 * | 11/2002 | Burke et al. ............ 606/198 |
| 6,488,705 B2 | 12/2002 | Schmitt et al. |
| 6,494,907 B1 * | 12/2002 | Bulver ................. 623/1.22 |
| 6,500,203 B1 | 12/2002 | Thompson et al. |
| 6,551,303 B1 | 4/2003 | VanTassel et al. |
| 6,599,308 B2 * | 7/2003 | Amplatz ................ 606/200 |
| 6,652,555 B1 | 11/2003 | VanTassel et al. |
| 6,652,556 B1 | 11/2003 | VanTassel et al. |
| 6,682,546 B2 | 1/2004 | Amplatz |
| 6,709,451 B1 | 3/2004 | Noble et al. |
| 6,709,455 B1 | 3/2004 | Chouinard |
| 6,730,108 B2 | 5/2004 | VanTassel et al. |
| 6,773,448 B2 | 8/2004 | Kusleika et al. |
| 6,830,576 B2 | 12/2004 | Fleischman et al. |
| 6,860,900 B2 | 3/2005 | Clerc et al. |
| 6,866,679 B2 | 3/2005 | Kusleika |
| 6,911,037 B2 | 6/2005 | Gainor et al. |
| 6,932,837 B2 | 8/2005 | Amplatz et al. |
| 6,949,113 B2 | 9/2005 | VanTassel et al. |
| 6,974,586 B2 | 12/2005 | Greenhalgh et al. |
| 7,025,779 B2 * | 4/2006 | Elliott ................. 623/1.35 |
| 7,029,494 B2 | 4/2006 | Soun et al. |
| 7,044,134 B2 | 5/2006 | Khairkhahan et al. |
| 7,052,513 B2 | 5/2006 | Thompson |
| 7,128,073 B1 | 10/2006 | van der Burg et al. |
| 7,147,656 B2 | 12/2006 | Andreas et al. |
| 7,152,605 B2 | 12/2006 | Khairkhahan et al. |
| 7,169,164 B2 | 1/2007 | Borillo et al. |
| 7,678,123 B2 | 3/2010 | Chanduszko |
| 8,621,975 B2 * | 1/2014 | Russo et al. ................ 87/9 |
| 2001/0000797 A1 | 5/2001 | Mazzocchi |
| 2001/0031981 A1 | 10/2001 | Evans et al. |
| 2002/0010481 A1 | 1/2002 | Jayaraman |
| 2002/0026237 A1 | 2/2002 | Schmitt et al. |
| 2002/0068950 A1 | 6/2002 | Corcoran et al. |
| 2002/0099437 A1 | 7/2002 | Anson et al. |
| 2002/0143349 A1 | 10/2002 | Gifford |
| 2002/0198584 A1 * | 12/2002 | Unsworth et al. ......... 623/1.11 |
| 2003/0055491 A1 | 3/2003 | Schwartz et al. |
| 2003/0057156 A1 | 3/2003 | Peterson et al. |
| 2003/0074019 A1 | 4/2003 | Gray et al. |
| 2003/0135265 A1 * | 7/2003 | Stinson ................. 623/1.16 |
| 2003/0135268 A1 * | 7/2003 | Desai .................. 623/1.19 |
| 2003/0167068 A1 | 9/2003 | Amplatz |
| 2003/0171770 A1 | 9/2003 | Kusleika et al. |
| 2003/0195553 A1 | 10/2003 | Wallace et al. |
| 2003/0199819 A1 | 10/2003 | Beck |
| 2004/0006363 A1 | 1/2004 | Schaefer |
| 2004/0093022 A9 | 5/2004 | Kurz et al. |
| 2004/0143293 A1 | 7/2004 | Marino et al. |
| 2004/0220610 A1 | 11/2004 | Kreidler et al. |
| 2005/0033321 A1 | 2/2005 | Fleischman et al. |
| 2005/0171572 A1 | 8/2005 | Martinez |
| 2005/0209633 A1 * | 9/2005 | Callister et al. ............ 606/200 |
| 2005/0209636 A1 | 9/2005 | Widomski et al. |
| 2005/0216049 A1 | 9/2005 | Jones et al. |
| 2005/0228434 A1 | 10/2005 | Amplatz et al. |
| 2005/0228489 A1 * | 10/2005 | Kujawski ................ 623/1.28 |
| 2006/0100684 A1 | 5/2006 | Elliott |
| 2006/0106419 A1 | 5/2006 | Gingras |
| 2006/0122645 A1 | 6/2006 | Brady et al. |
| 2006/0135947 A1 | 6/2006 | Soltesz et al. |
| 2006/0206201 A1 | 9/2006 | Garcia et al. |
| 2006/0224183 A1 | 10/2006 | Freudenthal |
| 2006/0241690 A1 | 10/2006 | Amplatz et al. |
| 2006/0247680 A1 | 11/2006 | Amplatz et al. |
| 2006/0253184 A1 | 11/2006 | Amplatz |
| 2006/0266474 A1 | 11/2006 | Burnside et al. |
| 2007/0043391 A1 | 2/2007 | Moszner et al. |
| 2007/0088384 A1 | 4/2007 | Vrba et al. |
| 2007/0112380 A1 | 5/2007 | Figulla et al. |
| 2007/0112381 A1 | 5/2007 | Figulla et al. |
| 2007/0167980 A1 | 7/2007 | Figulla et al. |
| 2007/0168018 A1 | 7/2007 | Amplatz et al. |
| 2007/0168019 A1 | 7/2007 | Amplatz et al. |
| 2007/0225760 A1 | 9/2007 | Moszner et al. |
| 2007/0265656 A1 | 11/2007 | Amplatz et al. |
| 2007/0265658 A1 | 11/2007 | Nelson et al. |
| 2008/0015628 A1 | 1/2008 | Dubrul et al. |
| 2008/0200945 A1 | 8/2008 | Amplatz et al. |
| 2008/0221554 A1 | 9/2008 | O'Connor et al. |
| 2009/0018562 A1 | 1/2009 | Amplatz et al. |
| 2009/0062841 A1 | 3/2009 | Amplatz et al. |
| 2009/0138072 A1 * | 5/2009 | Gendreau ................ 623/1.15 |
| 2009/0143814 A1 | 6/2009 | Gilson et al. |
| 2009/0171386 A1 | 7/2009 | Amplatz et al. |
| 2009/0187214 A1 | 7/2009 | Amplatz et al. |
| 2009/0210048 A1 | 8/2009 | Amplatz et al. |
| 2010/0030321 A1 * | 2/2010 | Mach .................. 623/1.18 |
| 2010/0121370 A1 | 5/2010 | Kariniemi |
| 2011/0184508 A2 * | 7/2011 | Burmeister et al. ......... 623/1.19 |
| 2013/0012979 A1 | 1/2013 | Amplatz et al. |
| 2013/0274866 A1 * | 10/2013 | Cox et al. ............... 623/1.18 |

FOREIGN PATENT DOCUMENTS

| | | |
|---|---|---|
| CN | 2613248 Y | 4/2004 |
| CN | 1736346 A | 2/2006 |
| DE | 103 38 702 B3 | 3/2005 |
| EP | 1 576 929 A2 | 9/2005 |
| JP | 4020308 U | 2/1992 |
| JP | 2001-515748 A | 9/2001 |
| JP | 2002-119515 A | 4/2002 |
| JP | 2005-261951 A | 9/2005 |
| JP | 2005-528181 A | 9/2005 |
| WO | WO 96/01599 A1 | 1/1996 |
| WO | WO 97/31672 | 9/1997 |
| WO | WO-97/42878 A1 | 11/1997 |
| WO | WO-98/47430 A1 | 10/1998 |
| WO | WO 99/12478 A1 | 3/1999 |
| WO | WO 99/39646 A1 | 8/1999 |
| WO | WO 00/13624 A2 | 3/2000 |
| WO | WO 00/28923 A1 | 5/2000 |

(56) References Cited

FOREIGN PATENT DOCUMENTS

| WO | WO 01/72367 A1 | 10/2001 |
| WO | WO-2004/064671 A2 | 8/2004 |
| WO | WO 2007/087005 A2 | 8/2007 |

OTHER PUBLICATIONS

United States Office Action for U.S. Appl. No. 11/820,841, dated May 2, 2013.
Chinese Office Action for Application No. 200880135936.2, dated Apr. 1, 2013.
Mexican Office Action for Application No. MX/a/2007/012825 dated Jun. 19, 2013.
U.S. Appl. No. 11/827,590, filed Jul. 12, 2007.
U.S. Appl. No. 11/966,397, filed Dec. 28, 2007, Adams et al.
Dictionary.com, definition of "plane", retrieved on Oct. 27, 2011 from <http://dictionary.com/browse/plane>; 5 pages.
Office Action for Mexican Application No. MX/a/2007/012825; dated Nov. 12, 2012.

* cited by examiner

STENT/STENT GRAFT FOR REINFORCEMENT OF VASCULAR ABNORMALITIES AND ASSOCIATED METHOD

BACKGROUND OF THE INVENTION

1) Field of the Invention

The present invention relates to an endovascular prosthesis and, in particular, to a stent/stent graft for treating vascular abnormalities, such as an aneurysm.

2) Description of Related Art

An aortic aneurysm is a weak area in the aorta, the main blood vessel that carries blood from the heart to the rest of the body. A common aneurysm is the abdominal aortic aneurysm ("AAA"), which may be caused by arteriosclerosis. As blood flows through the aorta, the weak vessel wall thins over time and expands like a balloon and can eventually burst if the vessel wall gets too thin. Most commonly, aortic aneurysms occur in the portion of the vessel below the renal artery origins. The aneurysm may be located in the vessels supplying the hips and pelvis, including the iliac arteries.

Once an aneurysm reaches about 5 cm in diameter, it is usually considered necessary to treat to prevent rupture. Below 5 cm, the risk of the aneurysm rupturing is lower than the risk of conventional heart surgery in patients with normal surgical risks. The goal of therapy for aneurysms is to prevent the aorta from rupturing. Once an AAA has ruptured, the chances of survival are low, with 80-90 percent of all ruptured aneurysms resulting in death. These deaths can be avoided if the aneurysm is detected and treated before it ruptures and ideally treated at an early stage (i.e., when the aneurysm is smaller than about 5 cm) with a lower risk procedure.

Aneurysms may be treated with surgery. The surgical procedure for treating AAA involves replacing the affected portion of the aorta with a synthetic graft, usually comprising a tube made out of an elastic material with properties very similar to that of a normal, healthy aorta. However, surgical treatment is complex and may pose additional risks to the patient, especially the elderly.

More recently, instead of performing surgery to repair an aneurysm, vascular surgeons have installed an endovascular prosthesis, (stent/stent graft) delivered to the site of the aneurysm using elongated catheters. The term "stent" refers to a device that is primarily metallic such a balloon or self expanding stent, where as the term "stent graft" refers to a device which comprises a combination of a stent and a natural or polymer fabric or a tubular member, thus the term "stent/stent graft" is used herein to include either configuration, both of which are used to support or line a vessel. Typically, the surgeon will make a small incision in the patient's groin area and then insert into the vasculature, a delivery catheter containing a collapsed, self-expanding or balloon-expandable stent/stent graft to a location bridging the aneurysm, at which point the stent/stent graft is delivered out from the distal end of the delivery catheter and expanded to approximately the normal diameter of the aorta at that location. Over time, the stent/stent graft becomes endothelialized and the space between the outer wall of the stent/stent graft and the aneurysm ultimately fills with clotted blood, which prevents the aneurysm from growing further since the stent/stent graft bypasses (excludes) the aneurysm and prohibits systematic pressure and flow on the weakened segment of the lumen.

Depending on where the aneurysm is in relation to other branch vessels, different design variations may be needed. For example, in treating AAA, the stent/stent graft should be placed so as not to occlude blood flow through the renal arteries which branch off from the abdominal aorta. Moreover, the stent/stent graft should be anchored within the lumen to reduce the incidence of migration, such as by promoting endothelialization or fixation with the lumen. Endoleaks may occur as a result of blood flowing around the stent, which may result in further weakening of the site of the aneurysm.

Furthermore, the size of the delivery catheter may affect the ability of the surgeon to manipulate the catheter within the lumen, often reduced in size due to arteriosclerosis, and may result in trauma to the vascular tissue. Thus, the smaller the delivery catheter, the less trauma to the tissue should occur, and the stent should be more easily and accurately positioned within the lumen. Smaller delivery catheters would also allow a physician access to smaller vessels, so as to more proactively treat aneurysms. Also, smaller aneurysms are typically easier to treat than larger aneurysms (e.g., aneurysms of at least 5 cm in diameter) because smaller aneurysms are more centrally located between the renal arteries and the iliac bifurcation and also because small aneurysms are more symmetrical and usually do not yet include tortuosity, nor involve the iliac arteries.

Conventional stent grafts are typically too bulky to be delivered to treat smaller aneurysms. For example, U.S. Pat. No. 5,800,508 to Goicoechea et al., U.S. Pat. No. 5,916,264 to Von Oepen et al., U.S. Pat. No. 6,110,198 to Fogarty et al., and U.S. Pat. No. 6,709,451 to Noble et al. disclose stent grafts for treating various vascular abnormalities. Although these stent grafts may be radially compressed for delivery, the stent grafts are not configured to be significantly constrained and elongated and may, thus, exhibit a bulkiness that prevents such stent grafts from being delivered to treat smaller aneurysms.

Therefore, there is a need for a stent/stent graft that is capable of being deployed within a variety of lumens for treating aneurysms. Moreover, there is a need for a stent/stent graft that may be easily delivered and adequately anchored within the lumen. There is a need for a stent/stent graft that can be placed in contact with the aneurysm wall, that facilitates tissue in-growth from the vessel wall to the stent/stent graft to strengthen the aneurysm wall and that resists further radial expansion. In addition, there is a need for a stent/stent graft that may be delivered within a lumen that is less traumatic to the vasculature and that may be used to prophylactically treat an aneurysm before becoming large enough to pose a significant health risk to the patient.

BRIEF SUMMARY OF THE INVENTION

Embodiments of the present invention may provide improvements over the prior art by, among other things, providing a stent/stent graft for treating vascular abnormalities, such as an aneurysm. For example, according to one embodiment, the stent/stent graft includes a flexible tubular structure including a proximal end and a distal end and having a heat set configuration. The tubular structure is heat set such that a portion between the proximal and distal ends of the tubular structure is configured to expand in response to an axial compressive force (or an outward radial force from the inside, e.g., blood pressure) to a diameter that is larger than a diameter at the proximal and distal ends of the tubular structure. Thus, the portion between the proximal and distal ends of the tubular structure may be configured to expand to, or slightly less than, a diameter of the vascular abnormality (e.g., an aneurysm), while the tubular structure may be configured to engage the lumen upstream and downstream of the aneurysm.

According to various aspects of the stent/stent graft, the tubular structure includes an expanded heat set configuration and is capable of being constrained to a smaller diameter than the expanded heat set configuration. The tubular structure may have a plurality of layers of braided strands (e.g., an elastic metallic alloy), and the layers may include respective tubular structures coaxially disposed in an overlying relationship. The tubular structure may be configured to be constrained to a diameter of less than about 10 French for delivery within a catheter. Moreover, a portion between the proximal and distal ends of the tubular structure may be larger than a diameter at the proximal and distal ends of the tubular structure prior to the tubular structure being expanded by an axial compressive force.

One aspect of the present invention provides a method for treating a vascular abnormality in a lumen. The method includes delivering a stent/stent graft proximate to the vascular abnormality in the lumen and axially compressing the stent/stent graft such that a portion of the stent/stent graft expands to a diameter that is larger than a diameter at the proximal and distal ends of the stent/stent graft. According to variations of the method, the axially compressing step includes axially compressing the stent/stent graft such that a portion of the stent/stent graft expands to about a diameter of the vascular abnormality. The method may further include constraining the stent/stent graft to a smaller diameter than an expanded heat set configuration, such as to a diameter of less than about 15 French. Furthermore, the stent/stent graft may include deploying the stent/stent graft within the lumen such that the stent/stent graft engages the lumen upstream and downstream of an aneurysm, wherein the axially compressing step includes axially compressing the stent/stent graft such that a portion between the proximal and distal ends of the stent/stent graft engages the aneurysm.

An additional embodiment of the present invention provides a stent/stent graft for treating an aneurysm within a lumen. The stent/stent graft includes a flexible tubular structure including a proximal end and a distal end and having a heat set configuration. The proximal and distal ends of the tubular structure are configured to engage the lumen upstream and downstream of the aneurysm, wherein a portion between the proximal and distal ends of the tubular structure is configured to at least partially conform to a contour of the aneurysm.

Aspects of the stent/stent graft include providing a tubular structure that includes an expanded heat set configuration having a first diameter and that may be configured to be constrained to a second diameter smaller than the expanded heat set configuration. For example, a ratio of the first diameter to the second diameter may be within the range of about 3:1 to 7:1. In addition, the tubular structure may be configured to be constrained to a diameter of less than about 15 French for delivery within a catheter. According to additional aspects of the stent/stent graft, the portion of the tubular structure may be configured to expand in response to an axial compressive force to a diameter that is larger than a diameter of the lumen upstream and downstream of the aneurysm. In addition, the tubular structure may include an expanded heat set configuration and be configured to be constrained to a smaller diameter than the expanded heat set configuration such that the portion of the tubular structure may be configured to self-expand to about the diameter of the aneurysm when unconstrained. Moreover, a portion between the proximal and distal ends of the tubular structure may be bulbous.

One embodiment of the present invention provides a method for treating an aneurysm in a lumen. The method includes delivering a stent/stent graft having proximal and distal ends proximate to an aneurysm in a lumen and deploying the stent/stent graft such that the proximal and distal ends of the stent/stent graft are configured to engage the lumen upstream and downstream of the aneurysm. A portion between the proximal and distal ends of the stent/stent graft is configured to at least partially conform to a contour of the aneurysm.

Various aspects of the method includes deploying the stent/stent graft such that the proximal and distal ends of the stent/stent graft expand to about a diameter of the lumen upstream and downstream of the aneurysm, and a portion between the proximal and distal ends of the stent/stent graft expands to about a diameter of the aneurysm. The method may further include axially compressing the stent/stent graft such that the portion of the stent/stent graft expands to a diameter that is larger than a diameter at the proximal and distal ends of the stent/stent graft. The method may also include constraining the stent/stent graft to a smaller diameter than an expanded heat set configuration.

An additional embodiment relates to a stent/stent graft for treating an aneurysm within a lumen, wherein the stent/stent graft includes a flexible tubular structure having a proximal end and a distal end configured to engage the lumen upstream and downstream of the aneurysm. A portion between the proximal and distal ends of the tubular structure is configured to at least partially conform to a contour of the aneurysm to promote endothelialization and re-enforcement of at least a portion of the aneurysm. Alternatively, a portion between the proximal and distal ends of the tubular structure may be configured to at least partially conform to a contour of the aneurysm and occlude blood flow therethrough.

BRIEF DESCRIPTION OF THE SEVERAL VIEWS OF THE DRAWINGS

Figure 1:
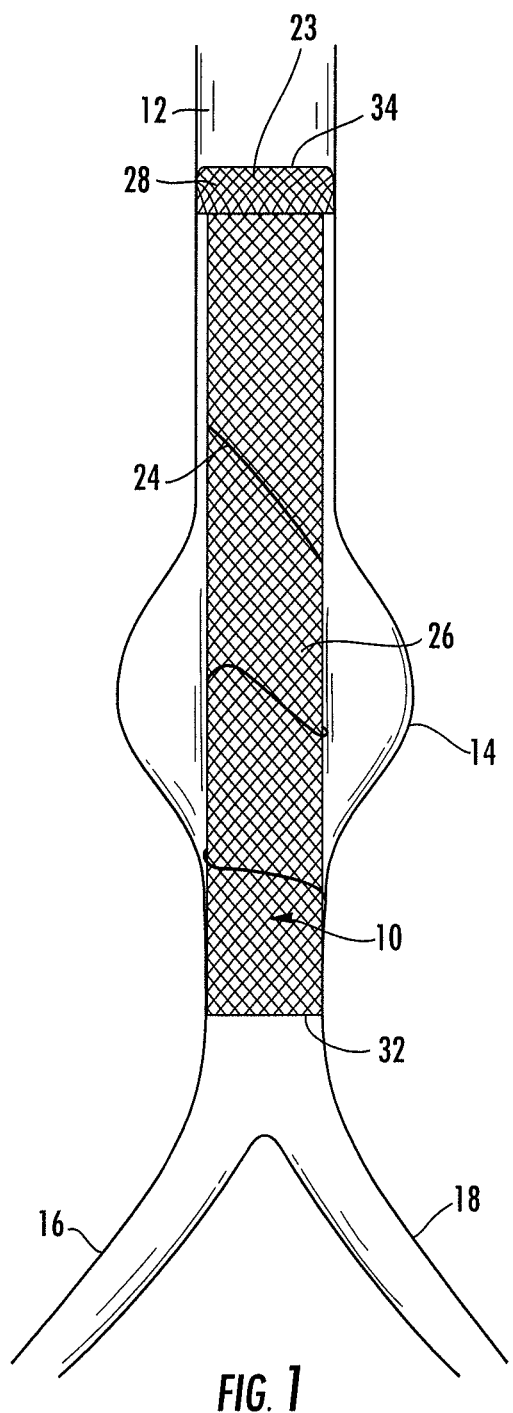
Figure 7:
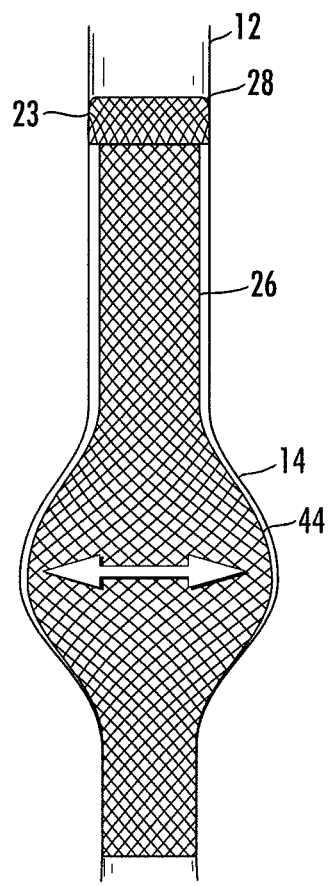
Figure 8:
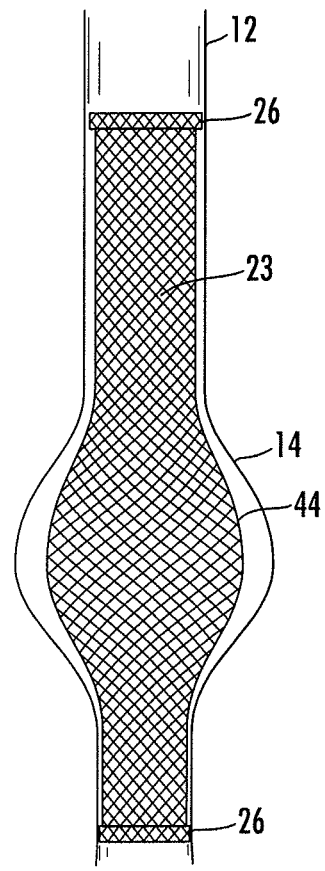
Figure 8A:
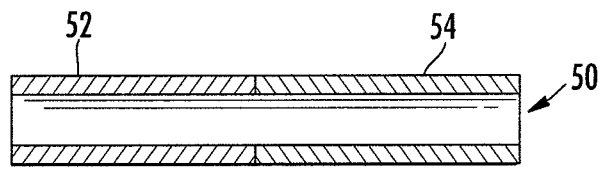
Figure 8B:
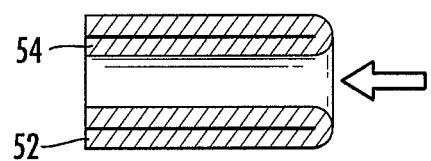
Figure 9:
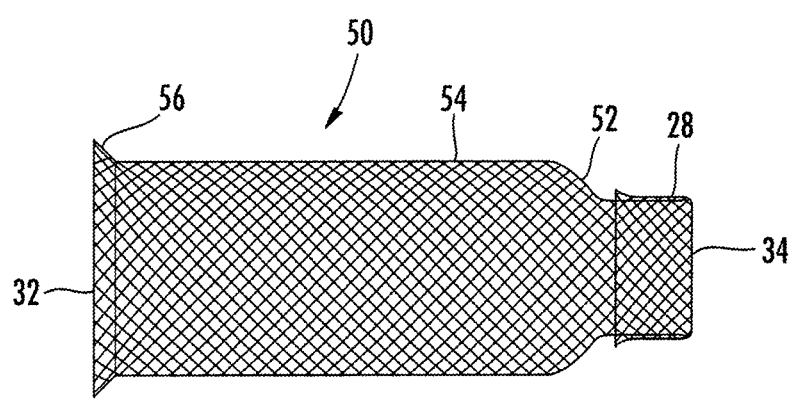

Having thus described the invention in general terms, reference will now be made to the accompanying drawings, which are not necessarily drawn to scale, and wherein:

FIG. 1 is a side elevational view of a stent stent/graft positioned within a lumen and bridging an aneurysm according to one embodiment of the present invention;

FIGS. 2-6 are side elevational views of a stent stent/graft being deployed from a catheter according to one embodiment of the present invention;

FIG. 7 is a side elevational view of a stent stent/graft positioned within a lumen according to another embodiment of the present invention;

FIG. 8 is a side elevational view of a stent stent/graft positioned within a lumen according to an embodiment of the present invention; and FIG. 9 is a side elevational view of a stent/stent graft according to an additional embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

With reference to FIG. 1, a stent/stent graft 10 is shown positioned within a lumen 12 having a vascular abnormality, such as an aneurysm 14. According to one embodiment, the lumen 12 is the abdominal aorta that branches into the left and right common iliac arteries 16 and 18. As illustrated in FIG. 1, the stent/stent graft 10 is configured to bridge the aneurysm 14 and includes a folded portion 28 that engages the lumen 12. As explained in further detail below, the folded portion 28 is configured to self expand and fold over upon itself to a heat set configuration so as to fixate the stent/stent graft within the lumen and provide additional hoop strength.

The term "vascular abnormality," as used herein is not meant to be limiting, as the stent/stent graft 10 may be configured to bridge or otherwise support a variety of vascular abnormalities. For example, the vascular abnormality could be any abnormality that affects the shape of the native lumen 12, such as an aneurysm, a lesion, a vessel dissection or a tumor. Furthermore, the term "lumen" is also not meant to be limiting, as the vascular abnormality may reside in a variety of locations within the vasculature, such as a vessel, an artery, a vein, a passageway, an organ, a cavity, or the like.

The stent/stent graft 10 may include one or more layers of occlusive material, wherein each layer comprises a tubular structure. The occlusive material may be any material that is configured to impede the flow of blood therethrough so as to facilitate thrombosis. According to one embodiment, FIG. 1 illustrates that an inner tubular member 23 may be coaxially disposed within an outer tubular member 26. The tubular structures 23, 26 comprise a plurality of braided strands, preferably of a shape memory metallic alloy, such as Nitinol. Thus, at least a portion of each of the tubular structures 23, 26 may be configured to self-expand and contact the lumen 12 so as to anchor the stent/stent graft 10 therein. The braid of the tubular structures 23, 26 may be chosen to have a predetermined pick and pitch to define openings or fenestrations so as to vary the impedance of blood flow therethrough. Although the term "strand" is discussed herein, "strand" is not meant to be limiting, as it is understood the braided tubular structure may comprise one or more wires, cords, fibers, filaments, cables, threads, or the like, such that such terms may be used interchangeably.

As used herein, "substantially preclude or impede flow" shall mean, functionally, that blood flow may occur for a short time, e.g., about 5-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the stent/stent graft and if no contrast media flows through the stent/stent graft wall after a predetermined period of time as viewed by fluoroscopy, then the position and occlusion of the stent/stent graft is adequate. Moreover, occlusion of the aneurysm 14 could be assessed using various echo modalities.

As used herein the term "proximal" shall mean closest to the operator (less into the body) and "distal" shall mean furthest from the operator (further into the body). In positioning of the stent/stent graft from a downstream access point, distal is more upstream and proximal is more downstream.

Moreover, the lengths of the tubular structures 23, 26 could also be varied with respect to one another. For example, the inner tubular structure 23 could be longer in length than the outer tubular structure 26 and include openings that are sufficiently large so as to occlude flow parallel to the wall but not to materially impede blood flow through its fenestrated wall, such as proximate to a branching artery. In addition, the tubular structures 23, 26 could comprise a plurality of wire strands and be braided so as to have a pick and pitch to define openings sufficiently small so as to substantially preclude blood flow therethrough, such as proximate to an aneurysm 14. Furthermore, even smaller fenestrations can be provided over at least a portion of the stent/stent graft 10 by having a third, outermost, tubular braided structure coaxially surrounding the outer tubular structure 26. Thus, the stent/stent graft 10 may include any number of layers of tubular structures (i.e., one or more) in order to achieve a desired amount of occlusive material and a desired size of fenestrations in specific portions of the stent/stent graft.

To achieve adequate fixation within the lumen, the diameter of the stent/stent graft 10 is configured to self expand to a diameter that is sized to be larger than, and exert an outward force against, and provide complete circumferential apposition to the diameter of the native lumen 12. For example, the stent/stent graft 10 diameter may be oversized in the range of 10-30%. Moreover, the stent/stent graft 10 may be oversized at the proximal 32 and/or distal 34 ends of the stent/stent graft 10 so as improve fixation within the lumen 12 upstream and/or downstream of the aneurysm 14.

According to one embodiment, each tubular structure 23 may comprise about 36-144 wire strands ranging in diameter from about 0.001 to 0.012 inches formed of a shape memory alloy, such as Nitinol, that are woven so as to exhibit fenestrations with an area of about 0.00015 to 0.1 sq. in., which are sufficiently small so as to slow the blood flow through the portion of the stent/stent graft 10 wall and to facilitate thrombus formation thereon. Inner and outer braided layers may have pitch rates that are about equal to obtain desirable collapse and expansion characteristics, such as maintaining a uniform overall length. According to one exemplary embodiment, the length of the inner tubular structure 23 is about 10 to 30 cm, and the length of the outer tubular segment 26 is about 8-18 cm, although the tubular structures may be various lengths, as described above. However, it is understood that in alternative embodiments, the tubular structures 23, 26 may be the same length, or the outer tubular structure may be longer than the inner tubular structure. According to one aspect of the present invention, the permeability through the composite wall of the stent/stent graft, composed of multiple layers, is greater than 100 cc/sq. cm/min. at 120 mm Hg. pressure. This porosity is greater than conventional stent/stent grafts and allows blood to temporarily flow easily through the graft wall, but the porosity is low enough to cause blood clotting between the vascular wall and the stent/stent graft, thereby promoting in growth of tissue into the openings of the stent/stent graft from the vascular wall to strengthen the vascular wall to resist any growth in the size of the aneurysm. The stent/stent graft internal wall later becomes covered with endothelial cells as in a natural artery.

The tubular structural layers 23, 26 may be coupled together using various techniques. For example, the tubular structures 23, 26 may be coupled using stitching, such as with platinum radiopaque wire strands. The stitching may be various sizes, such as having a diameter in the range of about 0.001 to 0.006 in. at one or more locations around the circumference the stent/stent graft 10, ideally positioned at a midpoint along the longitudinal axis. Using radiopaque wire strands facilitate visualization and positioning of the stent/stent graft within the lumen 12, as well as allows the multiple braided layers to freely move during collapse and expansion. By holding the layers together at or near the center of the stent/stent graft 10, the relative position of the layers in relation to one another may be substantially fixed, but the proximal 32 and distal 34 ends of the layers may have additional freedom to independently and fully expand.

It is understood that various connecting members other than stitching may be utilized to couple the tubular layers 23, 26 together. For example, one or more radial (helical) stitches 24 may be used to couple the tubular structures 23, 26 substantially along the length of the stent/stent graft, as shown in FIG. 1. The radial stitches 24 could be Nitinol and could be heat set at the same time the graft is heat set. Furthermore, stitching may also be placed at various locations other than the center of the stent/stent graft 10 such as spaced along the length of the stent/stent graft. In addition, other types of connecting members, such as sutures or radiopaque rivets may be used, or the geometry or wire engagement between the layers could be configured to engage one another.

It is also understood that the stent/stent graft may comprise various materials other than Nitinol that have elastic properties, such as spring stainless steel, trade named alloys such as Elgiloy, or Hastalloy, Phynox, MP35N, CoCrMo alloys or a mixture of metal and polymer fibers. Polymer fibers may include monofilaments or multifilament yarns ranging from about 10-400 denier. Individual filaments may range from about 0.25 to 10 denier. Polymers may be composed of PET (Dacron), polyester, polypropylene, polyethylene, HDPE, polyurethane, silicone, PTFE, polyolefins and ePTFE. The metal and plastic fibers may be combined in the same layer, or the tubular layers may be constructed in such a manner that each layer is made from a different material. The polymer layer may be a multifilament braided layer or may be composed of at least one filament or yarn wound about a mandrel with a pitch and diameter similar to other adjacent layers and may be positioned about or inside another adjacent layer or between adjacent layers. Depending on the individual material selected, the wire strand diameter, number of wire strands and pitch may be altered to achieve the desired properties of the stent/stent graft 10. Furthermore, the proximal 32 and/or distal 34 ends of the tubular members may flare radially outward (e.g., 10-30 degrees) from the longitudinal axis of the stent/stent graft 10 to improve end wire seating and anchoring in the lumen 12.

The stent/stent graft 10 may be various sizes and configurations. For example, the stent/stent graft 10 could include the following dimensions according to various aspects of the present invention:

| OD (mm) | EST'D COLLAPSED OD (inches) | EST'D COLLAPSED LENGTH (mm) |
| --- | --- | --- |
| 6 | 0.065 | 60 |
| 7 | 0.070 | 62 |
| 8 | 0.070 | 66 |
| 9 | 0.080 | 63 |
| 10 | 0.080 | 66 |
| 12 | 0.090 | 77 |
| 14 | 0.090 | 95 |

The outer diameter (OD) corresponds to the unconstrained OD of the stent/stent graft 10, while the collapsed OD and length may correspond to a size for delivery within a catheter, although such sizes may vary depending on the extent that the stent/stent graft is collapsed. According to a further aspect of the stent/stent graft 10, the stent/stent graft may be configured to fit within various sized catheters. For example, a stent/stent graft having an OD of about 17-23 mm may fit within a catheter having an inner diameter (ID) of about 0.150 inches, while a stent graft having an OD of about 24-26 mm may be carried by a catheter having an ID of about 0.163 inches.

For further details regarding the structure, exemplary dimensions, and method of making a stent/stent graft in accordance with additional aspects of the present invention, Applicants hereby incorporate by reference U.S. Patent Appl. Publ. No. 2007/0168018, filed on Jan. 13, 2006, and U.S. Patent Appl. Publ. No. 2007/0168019, filed on Jan. 17, 2007, herein in their entirety.

As briefly mentioned above, the stent/stent graft 10 is heat set such that at least a portion of the stent/stent graft is configured to self expand and fold over on itself to define a folded portion 28, as shown in FIG. 1. The folded portion 28 of the stent/stent graft is of slightly larger diameter than the remaining portion of the stent/stent graft 10. Thus, the folded portion 28 may facilitate fixation of the stent/stent graft within the lumen and prevent migration of the stent/stent graft following implantation.

According to one embodiment, the folded portion 28 is located at the distal end 34 of the stent/stent graft 10. Thus, the folded portion 28 may be located upstream of an aneurysm, such as in the abdominal aorta upstream of the left and right common iliac arteries 16 and 18, as shown in FIG. 1. However, it is understood that the stent/stent graft 10 could include one or more folded portions 28, such as at the proximal 32 and distal 34 ends of the stent/stent graft. In addition, the folded portion 28 may extend either inwardly within the lumen of the stent/stent graft 10 or outwardly to overlie the outer surface of the stent/stent graft. For example, the folded portion 28 may be at the proximal end 32 and folded inward due to the likelihood that an outward fold may get caught on the vessel wall before it has a chance to fold over since no portion would be retained within a delivery catheter. Moreover, the distal end 34 of the stent/stent graft 10 may have the wire ends flared slightly outward to help engage the vessel wall to prevent migration. Furthermore, the stent/stent graft 10 could be heat set such that a portion of the stent/stent graft between the proximal 32 and distal 34 ends could fold over on itself, such as a middle portion of the stent/stent graft to increase the hoop strength of the stent/stent graft 10 (e.g., in the region of a tumor or other abnormality that is restricting the lumen 12). The length of the folded portion 28 may vary depending on the amount of additional hoop strength and fixation desired, but is typically within the range of 15-40% of the diameter of the stent/stent graft 10 or 3-25% of the total length of the stent/stent graft.

Figure 2:
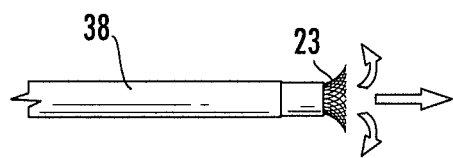
Figure 3:
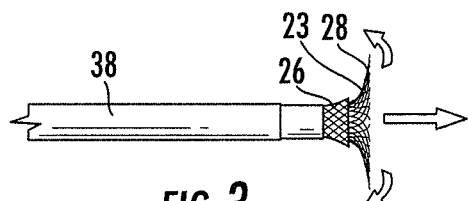
Figure 4:
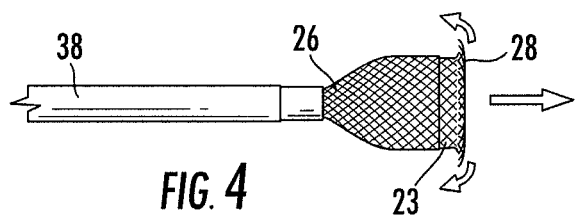
Figure 5:
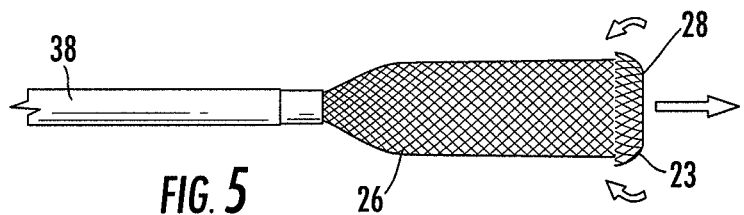
Figure 6:
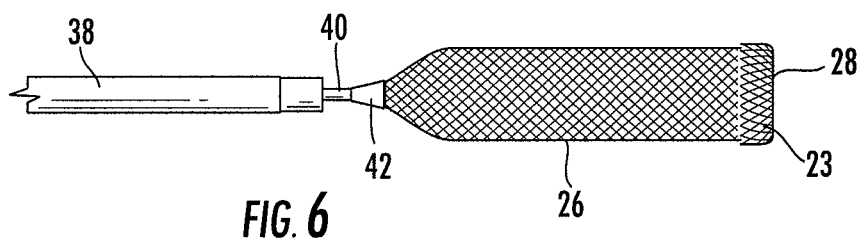

FIGS. 2-6 illustrate the progression of deployment of the stent/stent graft 10 from a delivery catheter 38. As shown in FIG. 2, when the distal end of the tubular structure 23 is deployed from the delivery catheter 38, the tubular structure 23 expands outwardly. Due to the propensity of the stent/stent graft 10 to return to its heat set configuration when released, the distal end 34 continues to fold outwardly and back, as shown in FIGS. 3-5. Thus, the distal end 34 of the tubular structure 23 expands outwardly about its circumference and folds back such that an inner surface of the tubular structure faces outwardly. Typically, the inner tubular structure 23 is of slightly longer length than the outer tubular structure 26, at least at the distal end 34 of the stent/stent graft, as shown in FIGS. 3 and 4. As such, the distal end 34 of the tubular structure 23 may fold over on itself or on itself and a portion of the distal end of the tubular structure 26 depending on the length of the folded portion and the differences in length between the tubular structures 23, 26. When the distal end 34 of the tubular structure 23 is completely released, the folded portion 28 has already returned to its heat set position, as illustrated in FIG. 6. Therefore, a portion of the inner surface of the tubular structure 23 defines the folded portion 28 and is configured to engage the lumen 12 about its circumference. When fully deployed and unconstrained, the folded portion 28 is configured to lie in intimate relationship with the underlying portion of the stent/stent graft 10 and the lumen 12 and may thereby provide additional hoop strength about the distal end 34 of the stent/stent graft and additional fixation within the lumen 12.

Various techniques could be employed to fabricate the stent/stent graft 10. According to one embodiment, the inner 23 and outer 26 tubular structures are braided to form a tubular fabric made of an elastic metallic material such as Nitinol. The outer braided tubular structure 26 would then be concentrically disposed over the inner tubular structure 23, and the combination would be placed about a cylindrical mandrel of the desired outer diameter for the stent/stent graft 10. One or more portions of the tubular structure 23 (e.g., the distal end 34) would be folded over upon itself to form one or more respective folded portions 28. This assembly would then be heated in a mold to a predetermined temperature and for a length of time sufficient to heat set the tubular structures to the diameter of the mandrel. Following removal from the mold, the two or more coaxial braided tubular structures 23, 26 may be held together by one or more connecting members, e.g., a radiopaque platinum wires or suture stitches. It is also contemplated that the stent/stent graft 10 may be coated with a drug-eluting polymer for promoting or inhibiting thrombus formation, promoting tissue in growth into the stent/stent graft or promotion of endothelial cells onto the stent/stent graft or other desired effects. The drug-eluting polymer may be selectively coated on the open weave or closed weave segments. For further details regarding exemplary techniques for fabricating a stent/stent graft 10, Applicants hereby incorporate by reference the contents of U.S. Pat. No. 6,123,715, filed Jul. 8, 1994, herein in its entirety.

In use, the stent/stent graft 10 would be deployed within the lumen in a compressed or constrained diameter that is smaller than its heat set diameter. Typically, the stent/stent graft 10 would be radially compressed or otherwise constrained to a smaller diameter and positioned within a delivery catheter 38 for delivery within the lumen. For instance, the stent/stent graft 10 may be constrained to a diameter of about 6-15 French. In addition, the ratio of the diameter of the expanded heat set configuration to the diameter of the constrained configuration may vary from, for example, about 3:1 to 7:1.

Furthermore, the stent/stent graft 10 may be releasably affixed at its proximal end 32 to a pusher catheter 40 via a clamp member 42. The stent/stent graft 10 would then be drawn into a lumen of an intravascular delivery catheter 38. The delivery catheter 38 would be introduced into the patient, such as by using the Seldinger technique, and then guided through the vascular system until a distal end of the delivery catheter is proximate to an aneurysm 14 to be treated. With the stent/stent graft 10 and the pusher catheter 40 held stationary, the delivery catheter 38 is withdrawn in the proximal direction to eject the stent/stent graft from the distal end of the delivery catheter where the distal end 34 of the stent/stent graft then self-expands to engage the lumen 12 with a portion of stent/stent graft bridging the aneurysm 14 being treated. The ends of the braided wire strands at the distal end 34 of the stent/stent graft dig into the walls, or otherwise engage, the lumen 12 (e.g., the folded portion may radially engage the lumen in the configuration shown in FIG. 3). The physician may then move the push catheter 40 slightly distally so as to begin to fold the distal end over on itself (e.g., the folded portion would resemble FIG. 4 at this stage). The delivery catheter 38 is then withdrawn proximally while holding the pusher catheter 40 stationary such that the fold back portion continues to fold over on itself to form the folded portion 28 (e.g., the folded portion may fold back on itself as shown in FIGS. 5 and 6). When the stent/stent graft 10 is fully deployed from the delivery catheter 38, the clamp member 42 is actuated so as to release the proximal end and allow the proximal end to self expand to contact the lumen 12. As shown in FIG. 1, the stent/stent graft 10 may be positioned such that the stent/stent graft bridges an aneurysm, with the folded portion 28 engaging the lumen 12 upstream of the aneurysm and the proximal end of the stent/stent graft engaging the lumen 12 downstream of the aneurysm. For further exemplary details regarding a delivery catheter, a pusher catheter, clamp member, and methods of using the same, Applicants hereby incorporate U.S. Patent Appl. Publ. No. 2006/0253184, filed May 4, 2005, herein in its entirety.

FIG. 7 depicts an additional embodiment of a stent/stent graft 10 that is configured to expand outwardly along a portion 44 between its proximal 32 and distal 34 ends. Thus, the stent/stent graft 10 may be configured to expand in the region of an aneurysm 14 such that the stent/stent graft not only engages the lumen 12 upstream and downstream of the aneurysm, but also at least partially conforms to the contour of the aneurysm. Thus, a portion (or preferably the majority) of the stent/stent graft 10 may be in intimate contact or proximate to the wall of the aneurysm 14 to promote endothelialization and in-growth around the stent/stent graft and ultimately prevent continued radial expansion of the aneurysm. Therefore, the stent/stent graft 10 is capable of reinforcing a weakened area of the lumen 12 and may eliminate the need for an additional fabric or braid material (e.g., polyester or Dacron material) needed to promote endothelialization and in-growth around the stent/stent graft 10, which may also reduce the size of the delivery catheter 38 needed to constrain the stent/stent graft since only the stent/stent graft scaffold is needed. For example, a delivery catheter 38 having an internal diameter of about less than 15 French may be used to constrain the stent/stent graft 10 therein, which also facilitates access to smaller lumens 12 and reduces procedural risks that may arise when delivering the stent/stent graft within the vasculature. Another potential advantage of the stent/stent graft 10 expanding to the aneurysm 14 is that the potential for endoleaks is eliminated because the aneurysm is not being bypassed and monitoring of the size of the aneurysm may be eliminated since the aneurysm would be reinforced and no longer able to grow. Additionally, because the stent/stent graft does not require a fabric covering, side branch arteries will remain patent reducing the chances of ischemia.

In order to obtain the configuration shown in FIG. 7, different portions of the stent/stent graft 10 may be heat set at different diameters. For example, a braided material could be fabricated on a mandrel having a first larger diameter (e.g., 30-35 mm), which is generally the maximum diameter to which the stent/stent graft would be capable of expanding. The braided material may then be pulled down or compressed onto a mandrel having a second smaller diameter (e.g., 20-25 mm) and heat set such that the heat set stent/stent graft is capable of self-expanding to the diameter of the second smaller diameter. However, when the stent/stent graft 10 is axially compressed, the stent/stent graft is capable of expanding to the first larger diameter. Thus, in order to deploy the stent/stent graft 10, the distal end 34 of the stent/stent graft 10 may be positioned distally of the aneurysm 14 and as the delivery catheter 38 is retracted, the distal end of the stent/stent graft engages the lumen 12. As the stent/stent graft is further deployed in the region of an aneurysm 14, the stent/stent graft may be axially compressed slightly by urging the delivery catheter 38 distally or by advancing the proximal end of the stent/stent graft distally to cause a portion 44 of the stent/stent graft to expand outwardly to conform to the contour of the aneurysm. The proximal end 32 of the stent/stent graft 10 may then be deployed to engage the lumen 12 downstream of the aneurysm 14. Thus, by maintaining axial compression with the delivery catheter 38 and or pusher catheter 40 during deployment of the distal end 24 of the stent/stent graft 10, the stent/stent graft may self-expand to conform to the aneurysm 14 and lumen 12. As a result, the stent/stent graft 10 will be in intimate contact along all or a substantial portion of its length in order to promote proliferation of cellular growth into the stent/stent graft and in time incorporate the stent/stent graft into the vessel 12 and aneurysm 14 walls.

It is understood that additional techniques may be employed to form the stent/stent graft 10 shown in FIG. 7. For example, a braided tubular material could be placed on a mandrel having a configuration of an aneurysm in the middle portion of the stent/stent graft such that the mandrel may have different diameters along its length. Thus, the stent/stent graft 10 could be heat set such that the stent/stent graft is configured to self expand from a constrained configuration and conform to the lumen 12 and aneurysm 14 as shown in FIG. 7. In addition, the stent/stent graft 10 may self expand and/or be axially compressed to have a bulbous configuration that is configured to at least partially or substantially conform to the shape of the aneurysm 14 (FIG. 7) or be less than a diameter of the aneurysm (FIG. 8). Similarly, the stent/stent graft 10 may include a bulbous portion 44 that is configured to be expanded further radially outwardly upon the application of an axial compressive force. For example, the stent/stent graft 10 shown in FIG. 8 could be axially compressed to obtain the configuration shown in FIG. 7.

FIG. 9 illustrates an additional embodiment of the present invention. The stent/stent graft 50 of FIG. 9 is "bullet" shaped and includes a folded portion 28 at its distal end 34 that is configured to be sized to engage the lumen 12. The stent/stent graft 50 includes a tapered portion 52 that extends between a cylindrical portion 54 and the folded portion 28. In addition, the stent/stent graft 50 includes a flared portion 56 at its proximal end 32 that is configured to anchor the stent/stent graft in the lumen 12. Thus, the stent/stent graft 50 is configured to substantially conform to an aneurysm 14, such as an early stage aneurysm that has not expanded significantly in diameter. In particular, the stent/stent graft 50 is configured to be form fitted to the aneurysm 14 in order to promote endothelialization around the stent/stent graft. As such, the stent/stent graft 50 may be embedded within the wall of the aneurysm over time so as to reinforce the aneurysm and prevent the aneurysm from expanding further.

In the case where the stent/stent graft 10 is positioned against the wall of the aneurysm 14, the bodily response is for tissue to grow into the open mesh of the stent/stent graft wall, such that the aneurysm wall is strengthened by the stent/stent graft wall. The fabrication of the stent/stent graft 10 may be such that at about the maximum aneurysm diameter or slightly larger than the diameter of the aneurysm, the stent/stent graft cannot expand further due to the helix angle being large relative to the stent/stent graft longitudinal axis. When axial compression from the proximal end 32 is necessary to expand the stent/stent graft 10 larger than its heat set memorized diameter, the ends of the stent/stent graft upstream and downstream of the aneurysm 14 may be sized relative to the native vessel 12 diameter to retain the stent/stent graft therein and to resist the tendency of the stent/stent graft to lengthen upon release. The proximal end 32 and/or distal end 34 of the stent/stent graft 10 may include hooks, may be flared, or may be folded as described above in order to aid in retention within the vessel 12.

Embodiments of the present invention may provide several advantages. For example, the folded portion 28 of the stent/stent graft 10 may provide additional fixation within the lumen 12 to reduce the incidence of migration. In this regard, the ends of the folded portion 28 may include ends of individual strands of braided material that dig into the lumen 12 prior to being folded over on itself or the ends may be heat set at an angle to the vessel wall to engage the wall. The folded portion 28 may also provide an increased diameter at the proximal 32 and/or distal 34 ends of the stent/stent graft 10 that may anchor the stent/stent graft within the lumen 12. In addition, the folded portion 28 may provide additional hoop strength around the circumference of the stent/stent graft so as to resist radial forces on the lumen 12, such as pressure from blood flowing through the stent/stent graft 10.

One embodiment provides a stent/stent graft 10 that includes an occluding material that may be used to prophylactically treat an aneurysm before becoming large enough to pose a health risk to the patient. In particular, because the stent/stent graft 10 may be constrained to be deployed within a delivery catheter 38 having a smaller inner diameter (e.g., less than 15 French), the stent/stent graft may be more easily delivered within smaller vessels and veins so as to proactively treat aneurysms or other vascular abnormalities before they pose a significant health risk. The occluding material also facilitates occlusion of the lumen 12 proximate to a vascular abnormality such that additional thrombogenic techniques may be unnecessary.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A stent/stent graft for treating a vascular abnormality in a lumen, the stent/stent graft comprising:
   a flexible tubular structure comprising a proximal end and a distal end, the flexible tubular structure having a heat set configuration and an expanded configuration, the heat set configuration having a heat set diameter and the expanded configuration having a maximum expandable diameter of the flexible tubular structure, wherein the flexible tubular structure is heat set in the heat set configuration such that the heat set diameter between the proximal and distal ends of the flexible tubular structure is larger than a diameter of at least one of the proximal or distal ends of the flexible tubular structure and is smaller than a maximum diameter of the vascular abnormality, and wherein the flexible tubular structure is configured to expand from the heat set diameter to the maximum expandable diameter in response to a distally directed axial compressive force such that the flexible tubular structure is configured to conform to the maximum diameter of the vascular abnormality.

2. The stent/stent graft of claim 1, wherein the flexible tubular structure is configured to be constrained from the heat set configuration to a smaller configuration than the heat set configuration and return to the heat set configuration when unconstrained.

3. The stent/stent graft of claim 1, wherein the flexible tubular structure comprises a plurality of layers, each of the plurality of layers comprising a plurality of braided strands.

4. The stent/stent graft of claim 3, wherein the plurality of layers comprise respective flexible tubular structures coaxially disposed in an overlying relationship.

5. The stent/stent graft of claim 3, wherein each of the plurality of layers comprises a plurality of braided strands of an elastic metallic alloy.

6. The stent/stent graft of claim 1, wherein the flexible tubular structure is configured to engage the lumen upstream and downstream of an aneurysm, and wherein a portion between the proximal and distal ends of the flexible tubular structure is configured to expand to about the maximum diameter of the aneurysm in response to the distally directed axial compressive force.

7. A stent/stent graft for treating a vascular abnormality within a lumen, the stent/stent graft comprising:
a flexible tubular structure comprising a proximal end and a distal end, the proximal and distal ends of the flexible tubular structure sized and configured to engage the lumen upstream and downstream of the vascular abnormality, the flexible tubular structure having a first heat set configuration and a second heat set configuration, the first heat set configuration having a first maximum heat set diameter and the second heat set configuration having a second maximum heat set diameter, wherein the first heat set configuration comprises different diameters along its length such that a portion between the proximal and distal ends of the flexible tubular structure corresponds to the first maximum heat set diameter and has a larger diameter than at least one of the proximal or distal ends of the flexible tubular structure, wherein the first maximum heat set diameter is less than both a maximum diameter of the vascular abnormality and the second maximum heat set diameter, and wherein the portion of the flexible tubular structure is configured to expand from the first maximum heat seat diameter to the second maximum heat set diameter to at least partially conform to the maximum diameter of the vascular abnormality.

8. The stent/stent graft of claim 7, wherein the flexible tubular structure is configured to be constrained to a diameter of less than about 15 French for delivery within a catheter.

9. The stent/stent graft of claim 7, wherein the flexible tubular structure is configured to be constrained to a diameter of less than about 12 French for delivery within a catheter.

10. The stent/stent graft of claim 7, wherein the flexible tubular structure is configured to be constrained to a diameter of less than about 10 French for delivery within a catheter.

11. The stent/stent graft of claim 7, wherein the flexible tubular structure is configured to be constrained to a diameter of less than about 8 French for delivery within a catheter.

12. The stent/stent graft of claim 7, wherein the portion between the proximal and distal ends of the flexible tubular structure is configured to expand from the first maximum heat set diameter to the second maximum heat set diameter in response to a distally directed axial compressive force.

13. The stent/stent graft of claim 7, wherein the flexible tubular structure is configured to be constrained to a smaller configuration than the first heat set configuration and return to the first heat set configuration when unconstrained.

14. The stent/stent graft of claim 13, wherein the flexible tubular structure has a reduced diameter when constrained to the smaller configuration from the first maximum heat set diameter, and wherein a ratio of the first maximum heat set diameter to the reduced diameter is within the range of about 3:1 to 7:1.

15. The stent/stent graft of claim 13, wherein the portion between the proximal and distal ends of the flexible tubular structure is configured to self-expand when unconstrained.

16. The stent/stent graft of claim 7, wherein the portion between the proximal and distal ends of the flexible tubular structure is bulbous.

17. The stent/stent graft of claim 7, wherein the portion between the proximal and distal ends of the flexible tubular structure is configured to substantially conform to a contour of the vascular abnormality along the entire length of the vascular abnormality.

18. A method for treating a vascular abnormality in a lumen, the method comprising:
delivering a stent/stent graft according to claim 1 proximate to the vascular abnormality in the lumen; and
axially compressing the stent/stent graft in a distal direction such that the flexible tubular structure expands from the maximum heat set diameter to the maximum expandable diameter to conform to the maximum diameter of the vascular abnormality.

19. The method of claim 18, further comprising constraining the stent/stent graft to a smaller diameter than the heat set configuration.

20. The method of claim 19, wherein constraining comprises radially compressing the stent/stent graft to a diameter of less than about 15 French.

21. The method of claim 18, further comprising deploying the stent/stent graft within the lumen such that the stent/stent graft engages the lumen upstream and downstream of a vascular abnormality, and wherein axially compressing comprises axially compressing the stent/stent graft such that a portion between the proximal and distal ends of the stent/stent graft engages the vascular abnormality.

22. A method for treating a vascular abnormality in a lumen, the method comprising:
delivering a stent/stent graft according to claim 7 proximate to the vascular abnormality in a lumen; and
deploying the stent/stent graft such that the proximal and distal ends of the the flexible tubular structure engage the lumen upstream and downstream of the vascular abnormality and the portion between the proximal and distal ends of the the flexible tubular structure at least partially conforms to a contour of the vascular abnormality.

23. The method of claim 22, wherein deploying comprises deploying the stent/stent graft such that the proximal and distal ends of the flexible tubular structure expand to about a diameter of the lumen upstream and downstream of the vascular abnormality, and the portion between the proximal and distal ends of the graft flexible tubular structure expands to about the maximum diameter of the vascular abnormality.

24. The method of claim 23, further comprising axially compressing the stent/stent graft in a distal direction such that the first maximum heat set diameter of the graft the flexible tubular structure further expands to the second maximum heat set diameter of the flexible tubular structure.

25. The method of claim 23, further comprising constraining the stent/stent graft to a smaller configuration than the first heat set configuration.

26. A stent/stent graft for treating an aneurysm within a lumen, the stent/stent graft comprising:
a flexible tubular structure comprising a proximal end and a distal end configured to engage the lumen upstream and downstream of the aneurysm, wherein the flexible tubular structure is heat set to include different diameters along its length in a relaxed state such that a portion between the proximal and distal ends of the flexible tubular structure has a larger diameter than at least one end of the tubular structure, wherein the maximum heat set diameter of the flexible tubular structure is less than a maximum diameter of the aneurysm, and wherein the flexible tubular structure is configured to conform to a contour of the aneurysm along the entire length of the aneurysm in response to a distally directed axial compressive force to promote endothelialization and re-enforcement of the aneurysm.

27. A stent/stent graft for treating an aneurysm within a lumen, the stent/stent graft comprising:
a flexible tubular structure comprising a proximal end and a distal end configured to engage the lumen upstream and downstream of the aneurysm, wherein the flexible tubular structure is heat set to include different diameters along its length in a relaxed state such that a portion between the proximal and distal ends of the flexible tubular structure has a larger diameter than at least one end of the flexible tubular structure, wherein a maximum heat set diameter of the flexible tubular structure is less than a maximum diameter of the aneurysm, and wherein the flexible tubular structure is configured to conform to a contour of the aneurysm along the entire length of the aneurysm in response to a distally directed axial compressive force and to occlude blood flow therethrough.

28. The stent/stent graft of claim 27, wherein the portion between the proximal and distal ends of the flexible tubular structure is configured to be at least partially endothelialized.

29. The stent/stent graft of claim 27, wherein the portion between the proximal and distal ends of the flexible tubular structure is configured to be substantially endothelialized.

30. A stent/stent graft for treating a vascular aneurysm comprising:
a tubular structure comprising elastic braided metal strands and having a proximal end and a distal end, wherein the tubular structure is heat set to include different diameters along its length in a relaxed state such that a portion of the tubular structure between the proximal and distal ends has a larger diameter than at least one end of the tubular structure, wherein the maximum heat set diameter is less than a maximum diameter of the aneurysm, and wherein the tubular structure is configured to be placed within the aneurysm such that the maximum heat set diameter conforms to the maximum diameter of the aneurysm in response to a distally directed axial compressive force.

31. The stent/stent graft of claim 30, wherein the tubular structure comprises one or more polymer strands.

32. The stent/stent graft of claim 30, wherein the tubular structure comprises a plurality of layers, wherein at least one layer comprises elastic braided metal strands and at least one other layer comprises braided polymer strands.

33. The stent/stent graft of claim 1, wherein the flexible tubular structure comprises at least one layer of braided strands.

34. The stent/stent graft of claim 33, wherein the at least one layer of braided strands comprises an elastic metallic alloy.

35. The stent/stent graft of claim 1, wherein the flexible tubular structure is heat set in the expanded configuration.

36. The stent/stent graft of claim 33, wherein the flexible tubular structure is braided between its proximal and distal ends at a predetermined helix angle, and wherein the maximum expandable diameter is limited by the helix angle.

37. The stent/stent graft of claim 7, wherein the flexible tubular structure comprises strands braided between its proximal and distal ends at a predetermined helix angle, and wherein the maximum expandable diameter is limited by the helix angle.

38. The stent/stent graft of claim 1, wherein a ratio of the maximum expandable diameter to the maximum heat set diameter is about 1.4 to 1.5.

* * * * *